United States Patent [19]

Schottenfeld

[11] Patent Number: 5,562,328
[45] Date of Patent: Oct. 8, 1996

[54] TOY NOVELTY DISPENSER VEHICLE

[76] Inventor: Barbara Schottenfeld, 175 W. 12th St., New York, N.Y. 10011

[21] Appl. No.: 482,124

[22] Filed: Jun. 7, 1995

Related U.S. Application Data

[63] Continuation-in-part of Ser. No. 408,080, Mar. 22, 1995, abandoned.

[51] Int. Cl.⁶ ................................ G07F 11/00; B65G 1/04
[52] U.S. Cl. ........................... 312/35; 221/248; 221/250; 221/199; 221/279; 221/97; 221/99; 221/100; 221/282; 221/24; 446/310; 446/475
[58] Field of Search ................................. 221/247, 248, 221/249, 24, 199, 152, 154, 279, 280, 282, 97, 99, 100, 103, 226, 250; 206/69, 556; 446/310, 6, 475; 312/204, 35; 211/51, 59.3

[56] References Cited

U.S. PATENT DOCUMENTS

| | | | |
|---|---|---|---|
| 874,416 | 12/1907 | Mont | 221/24 X |
| 896,263 | 8/1908 | Aagland | 221/24 X |
| 2,449,116 | 9/1948 | Hatchett | 446/310 X |
| 2,519,438 | 8/1950 | Conley | 221/269 X |
| 4,836,821 | 6/1989 | Raymond | 446/475 X |
| 5,071,033 | 12/1991 | Siwek | 221/247 X |
| 5,120,263 | 6/1992 | Ierfino et al. | 446/310 X |
| 5,178,298 | 1/1993 | Allina | 221/24 |
| 5,310,084 | 5/1994 | Pittman | 221/199 X |
| 5,435,459 | 7/1995 | Huck et al. | 221/70 |
| 5,447,253 | 9/1995 | Williams | 221/92 |

FOREIGN PATENT DOCUMENTS

| | | | |
|---|---|---|---|
| 746559 | 3/1933 | France | 221/24 X |
| 8301330 | 4/1983 | WIPO | 221/24 X |

Primary Examiner—H. Grant Skaggs
Assistant Examiner—Dean A. Reichard
Attorney, Agent, or Firm—Kuhn and Muller

[57] ABSTRACT

A novelty dispenser for solid objects, such as condoms. The novel features are specifically based on a spring loaded movement of a dispensing element, which element moves an object such as a packaged condom from inside a compartment out through an opening. The dispenser is an everyday entertainment device that conceals a condom therein. It uses a spring, such as a coil spring, which feeds the condom from a magazine compartment and through a shutter to be released for use. The spring is returned to its original position once it has been used. Pulling a tab of the dispenser causes the spring to release within the magazine, forcing the condom through the shutter, such as miniature doors. The spring opens the magazine and doors, allowing the spring to advance the condom into the dispensed position for delivery to the user.

15 Claims, 16 Drawing Sheets

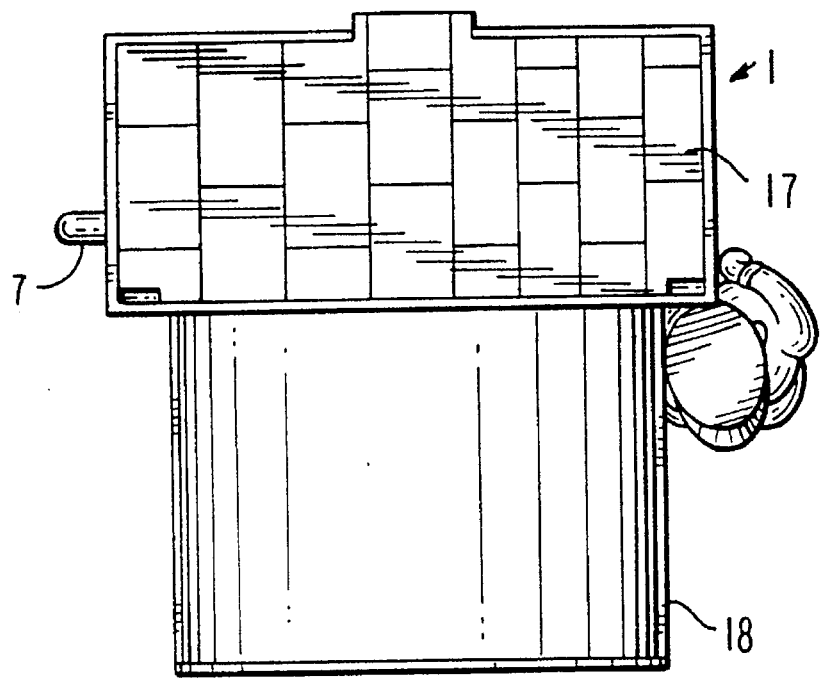
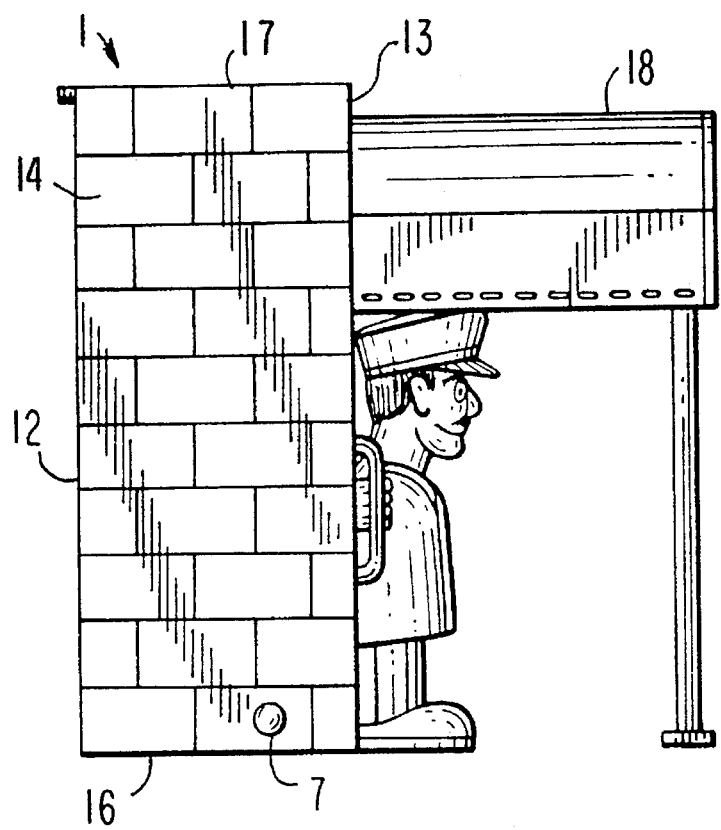

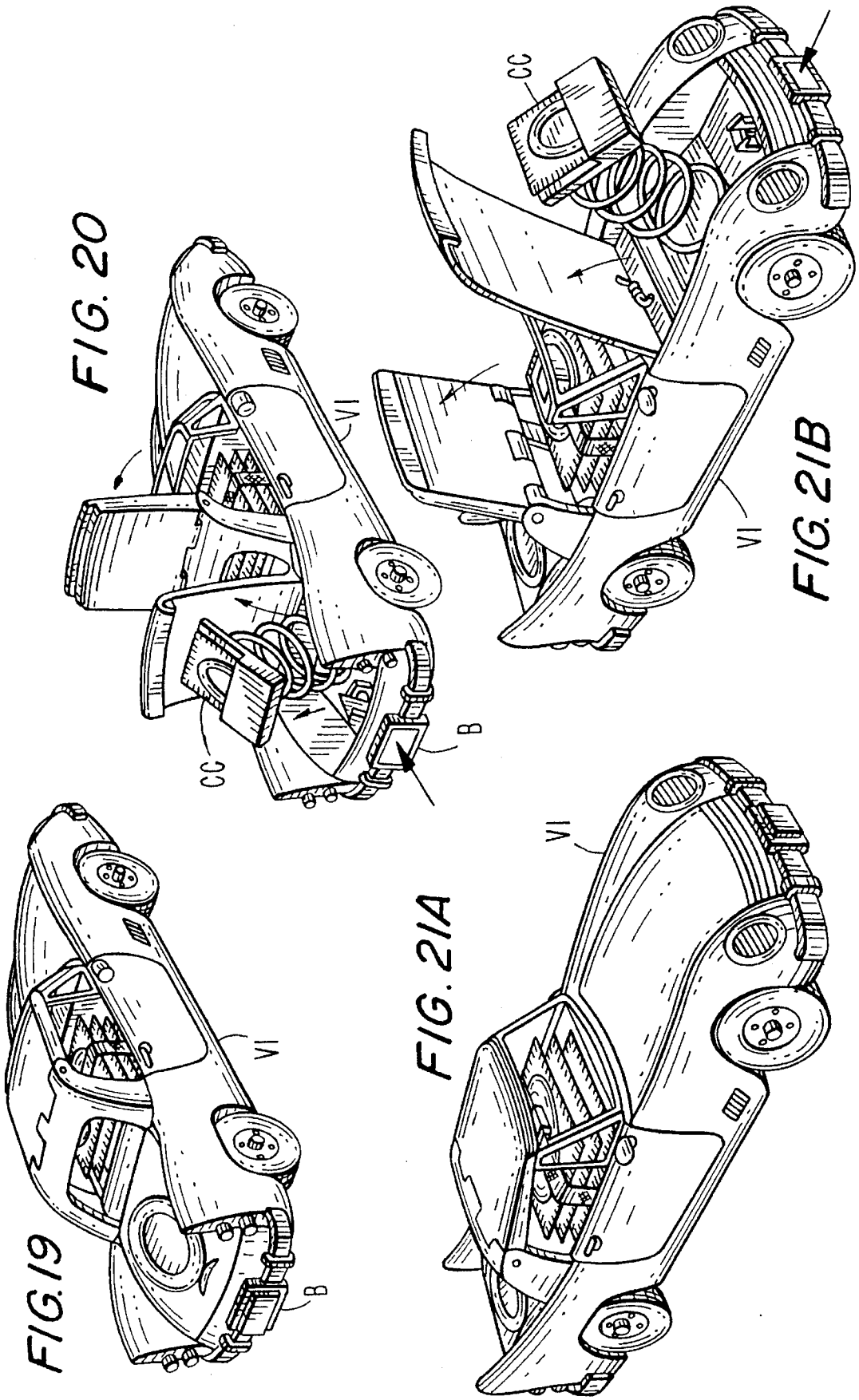

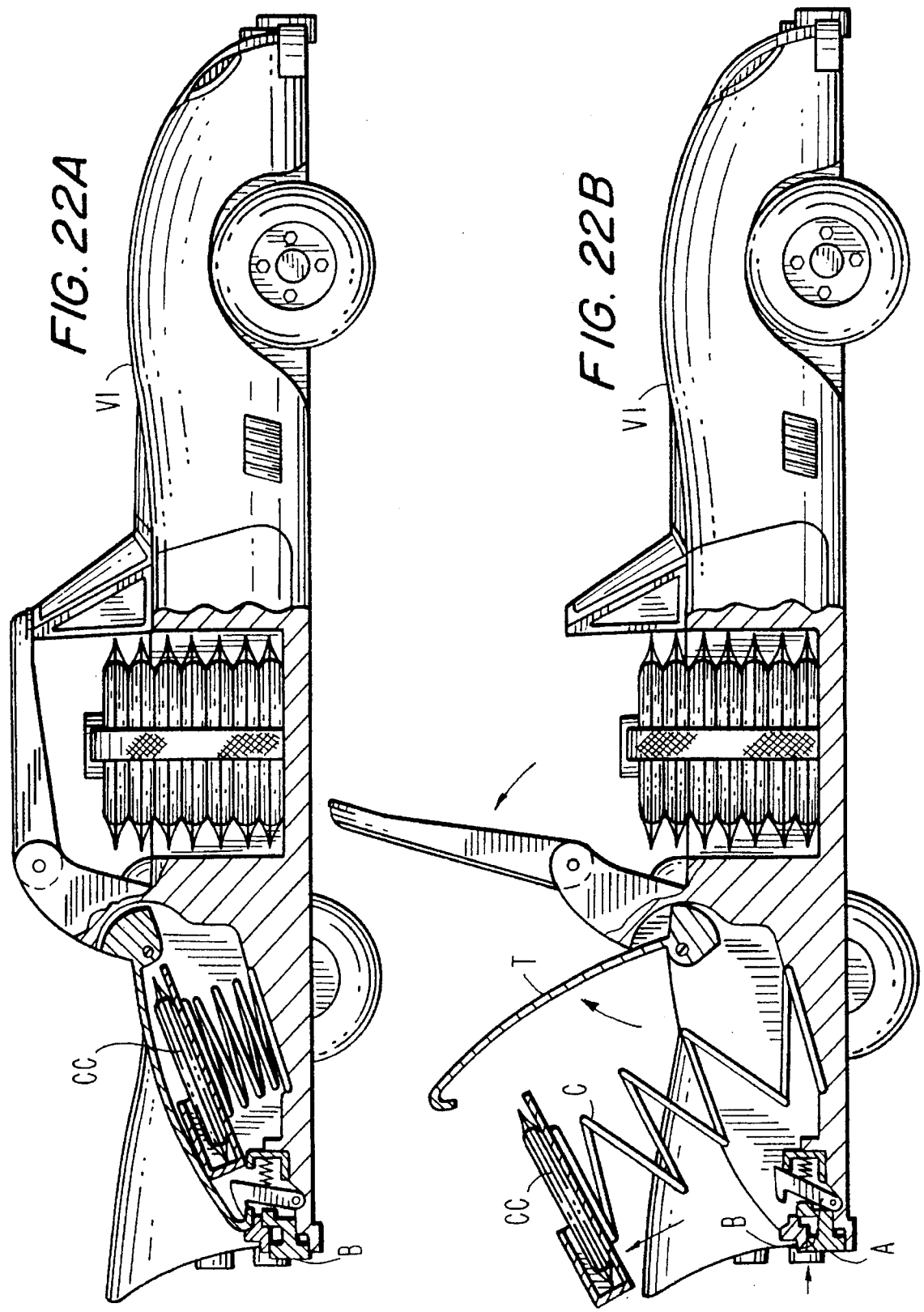

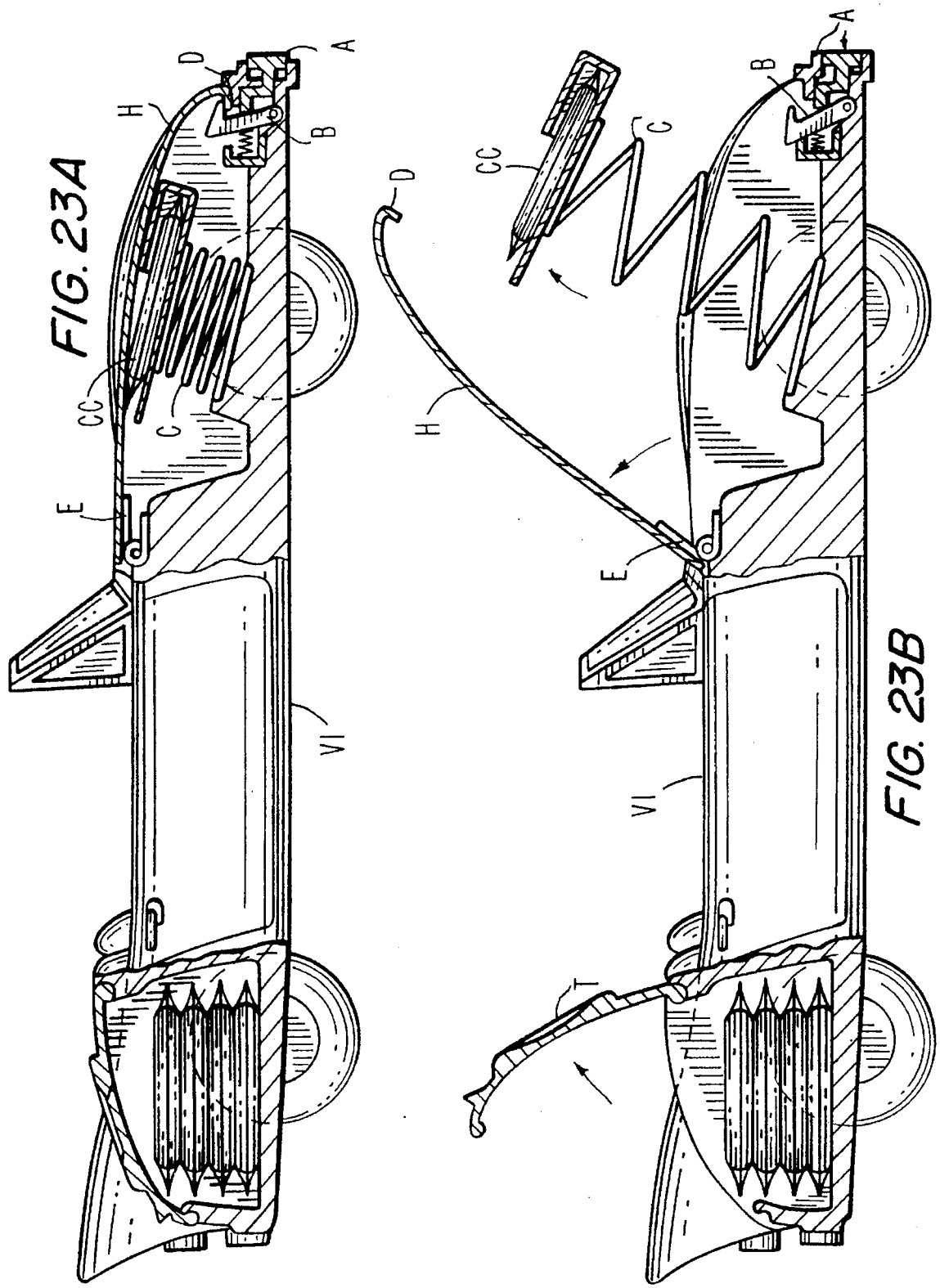

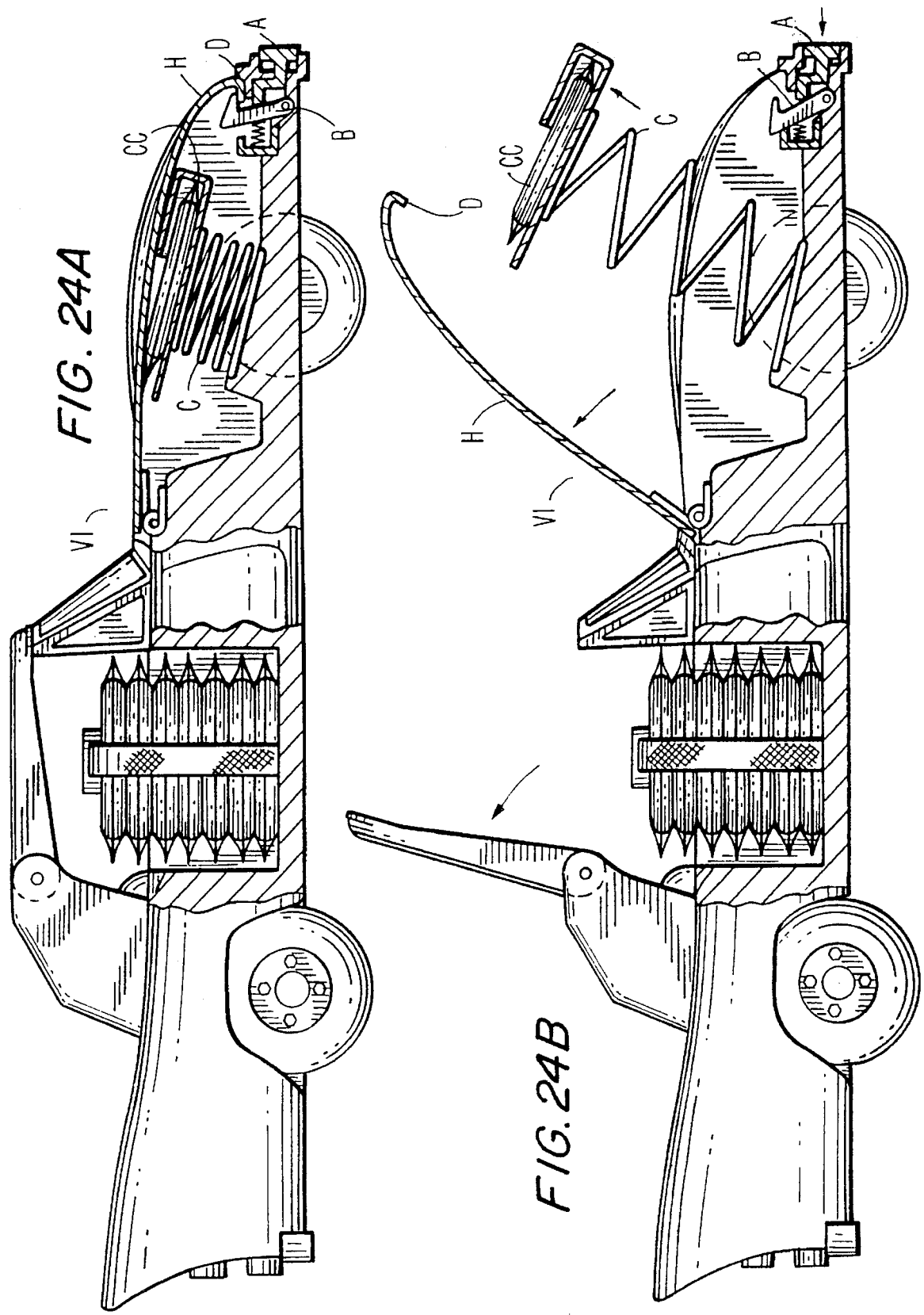

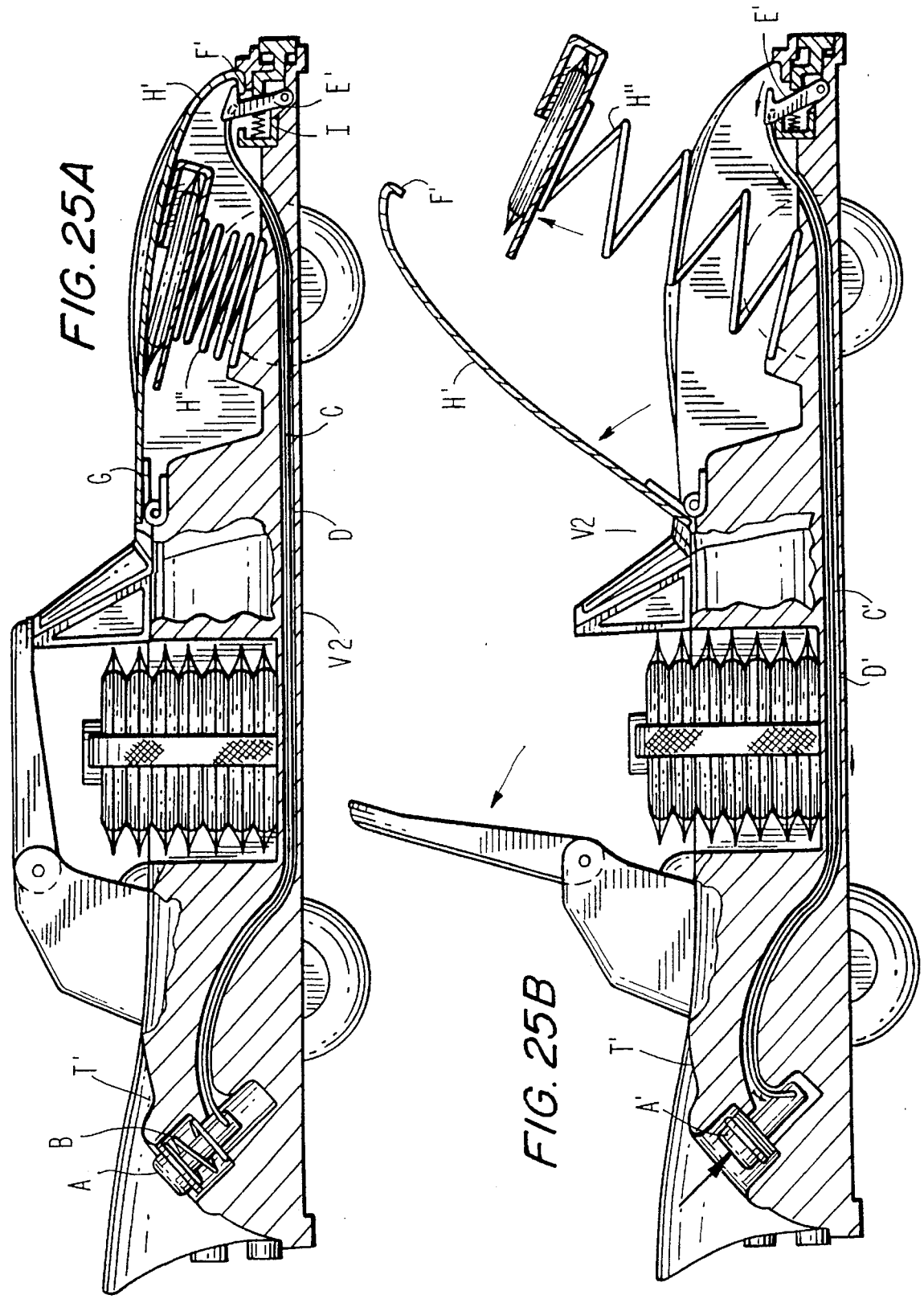

5,562,328

1

TOY NOVELTY DISPENSER VEHICLE

This application is a continuation-in-part of application Ser. No. 08/408,080, filed on Mar. 22, 1995 abandoned.

BACKGROUND OF THE INVENTION

The main object of the present invention is to provide a novel dispenser for solid objects such as packaged condoms. The novel features are specifically based on a spring loaded movement of a dispensing element, which element moves a condom package from inside a compartment through an opening.

More precisely, the present invention concerns an entertainment device which also functions as a condom package dispenser.

The dispenser is an everyday novelty device that conceals a condom within an ingenious arrangement. It uses a spring, such as a coil spring, which feeds the condom package from a magazine compartment, and the spring is returned to its original position once it has been used. Pulling a tab of the dispenser causes the spring to release within the magazine compartment, forcing the condom through an operable shutter, such as one or more doors. The spring opens the magazine compartment and doors, allowing the spring to advance the condom into the dispensed position.

In loading, a condom is fed into the magazine compartment of the dispenser and held there by a coil spring that advances the condom from the magazine compartment.

OBJECTS OF THE INVENTION

It is an object of the present invention to provide a discrete dispenser for dispensing objects, such as condom packages.

A further object of the present invention is to provide a quick and convenient method of dispensing a condom.

It is yet another object to provide a container for discretely concealing condom packages therein.

SUMMARY OF THE INVENTION

In keeping with these objects and others which may become apparent, the present invention includes a dispensing device for solid objects, such as condom packages.

The dispensing device for condoms can be used by simply moving a lever or pulling a tab to open a slidably movable cover, such as at least one door sleeve or shutter to the indicated extent for release of the condom.

The present invention includes three separate parts. One part includes a magazine compartment holding a condom package therein. A holder is attached to a central spring which fits into an openable cabinet or other housing structure, such as a miniature building, a condiment jar or toy vehicle.

Extra condoms can be stored within the top of the dispenser.

The solid objects, such as a condom package, are housed in the space between the spring and a holding restraining shutter, such as a door, which may be a hingably movable outer cover, enclosing an opening in the housing structure. The shutter holds the condom package within the magazine.

By using the thumb and forefinger of one hand on a tab or other conventional finger friction means removably attachable to the slidable outer shutter, such as a door, and pulling the tab out, the opening to the magazine can be easily exposed. The spring is used to move the condom out from the dispenser. The condom moves through the opening of the hollow inner magazine of the dispenser.

DETAILED DESCRIPTION OF THE DRAWINGS:

The present invention can best be understood in conjunction with the following drawing figures in which:

FIG. 2 is a top plan view thereof;

FIG. 3 is a left side elevational view thereof;

FIG. 19 is a perspective view of a fourth embodiment of the present invention.

FIG. 20 is a perspective view thereof in an open position.

FIGS. 21A and 21B are perspective views of a fifth embodiment in closed and open positions respectively.

FIGS. 22A and 22B are side elevation views in partial section of a sixth embodiment of the present invention.

FIGS. 23A and 23B are side elevation views in partial section of a seventh embodiment of the present invention.

FIGS. 24A and 24B are side elevational views in partial section of an eighth embodiment of the present invention.

FIGS. 25A and 25B are side elevation views in partial section of a ninth embodiment of the present invention.

DETAILED DESCRIPTION OF THE PREFERRED EMBODIMENT

Figure 1:
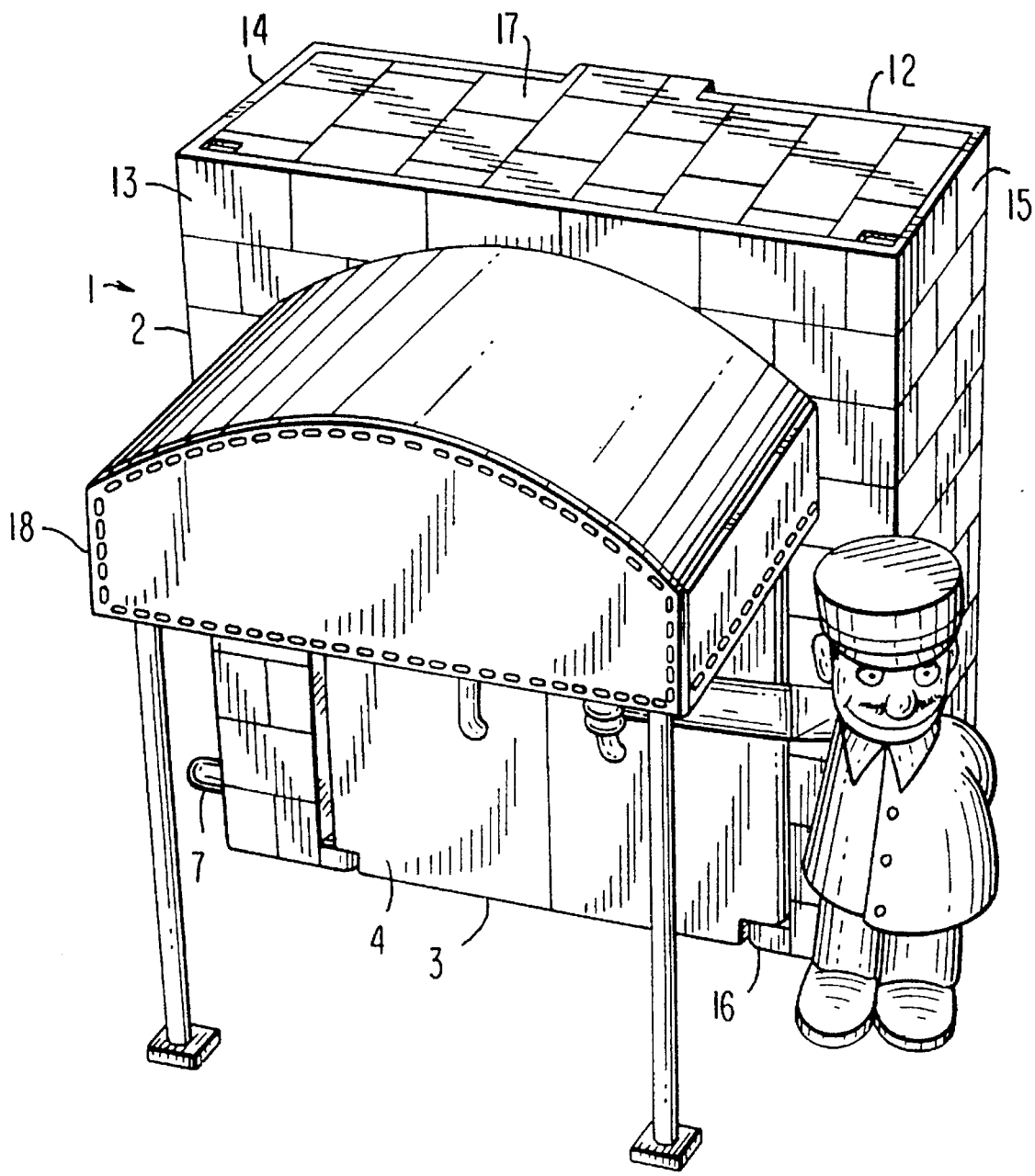
FIG. 1 is a perspective view of the novelty dispenser of the present invention.
Figure 5:
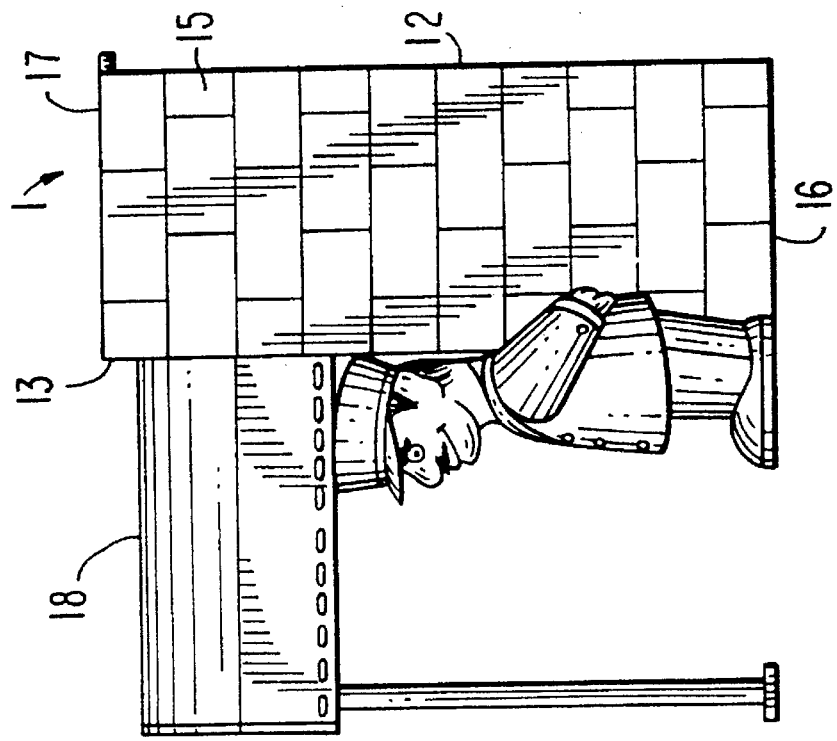
FIG. 5 is a right side elevational view thereof.
Figure 4:
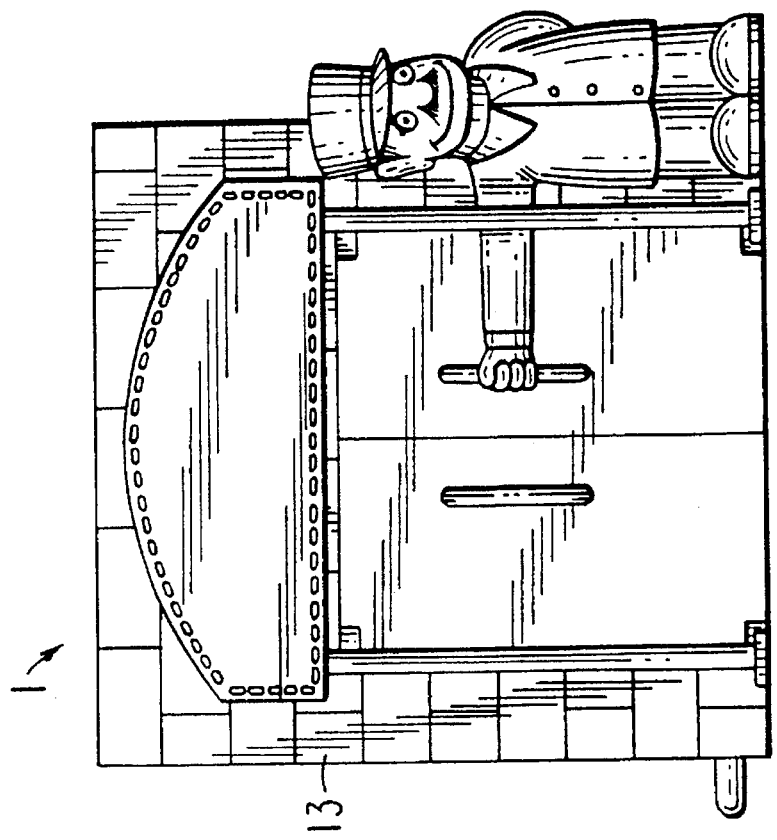
FIG. 4 is a front elevational view thereof.
Figure 6:
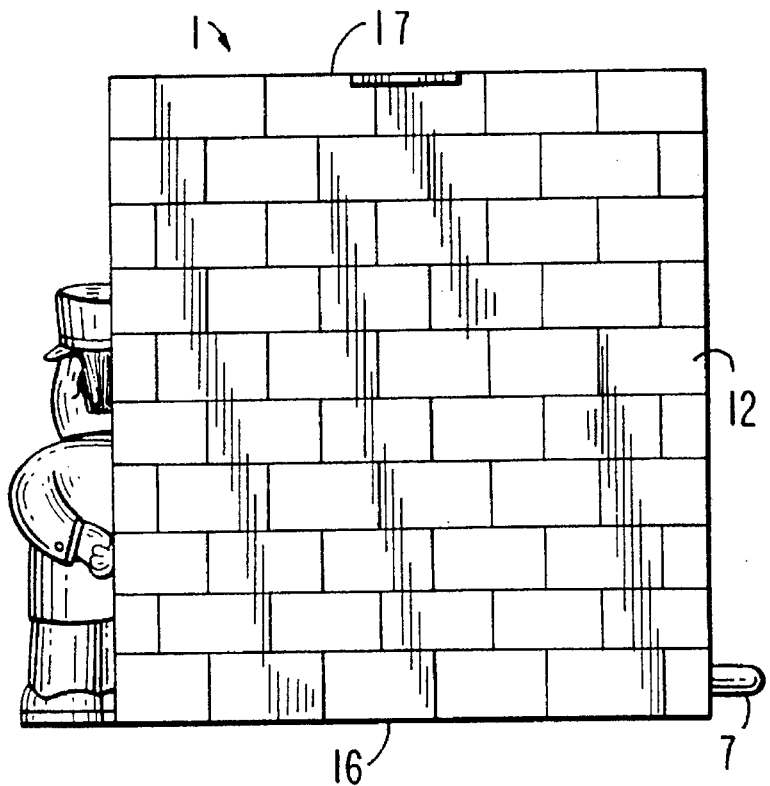
FIG. 6 is a rear view thereof.
Figure 7:
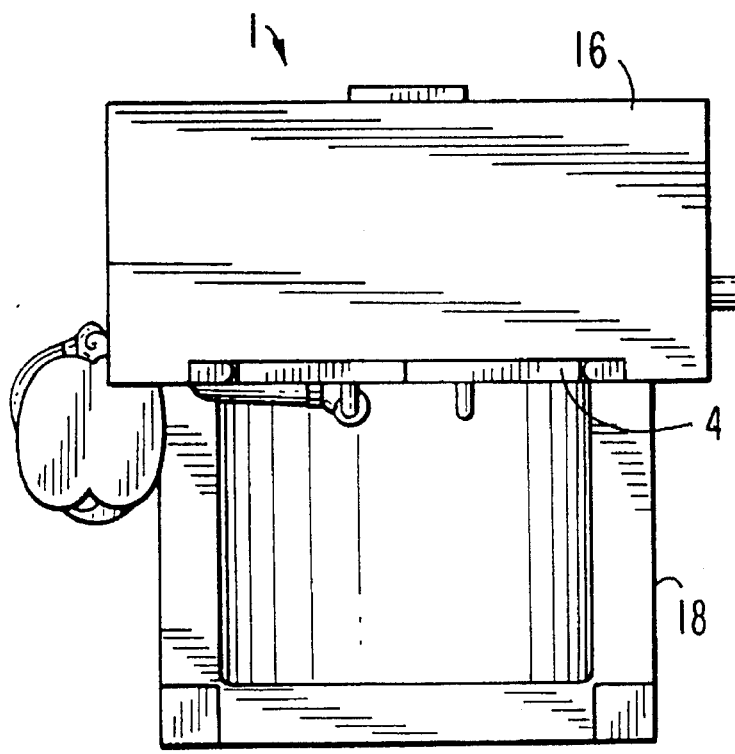
FIG. 7 is a bottom view thereof.
Figure 8:
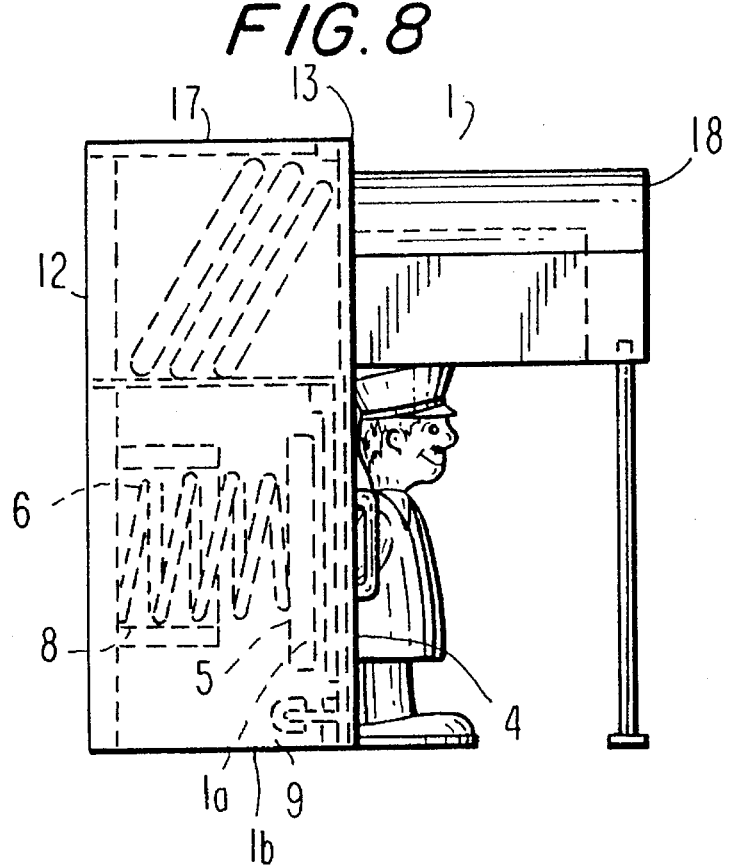
FIG. 8 is a left side view thereof with internal parts shown in dotted lines.
Figure 9:
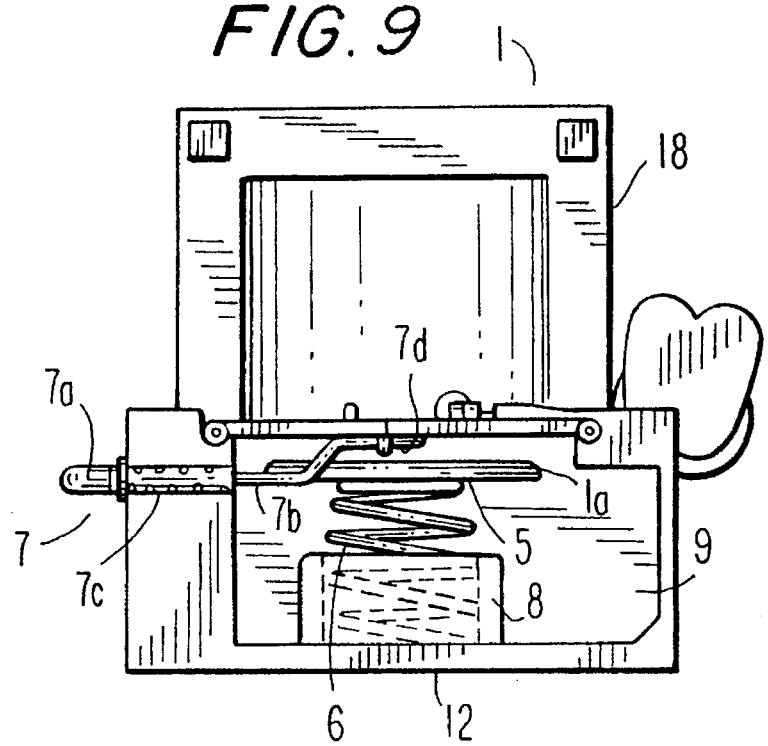
FIG. 9 is a bottom view thereof, with internal parts shown in partial section.
Figure 10:
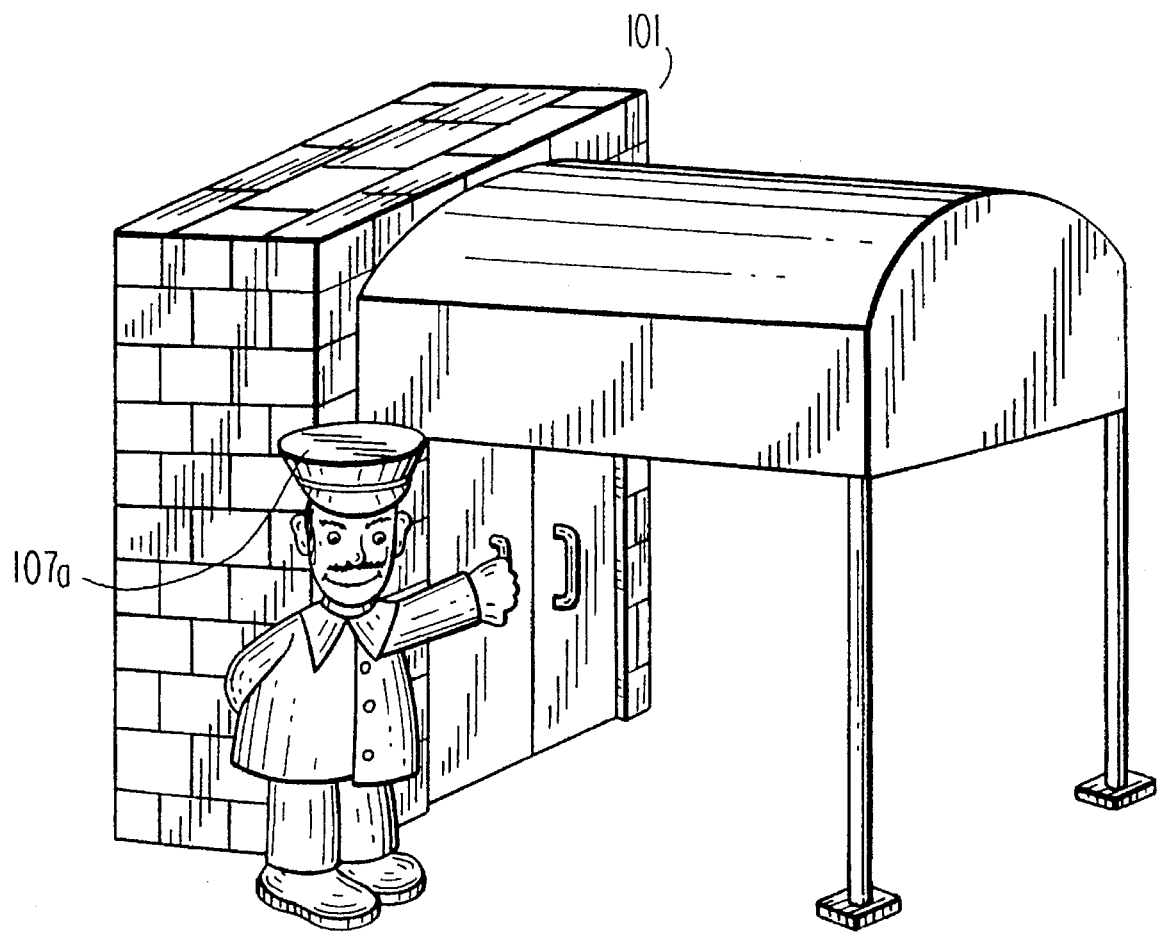
FIG. 10 is a perspective view of an alternate embodiment.
Figure 11:
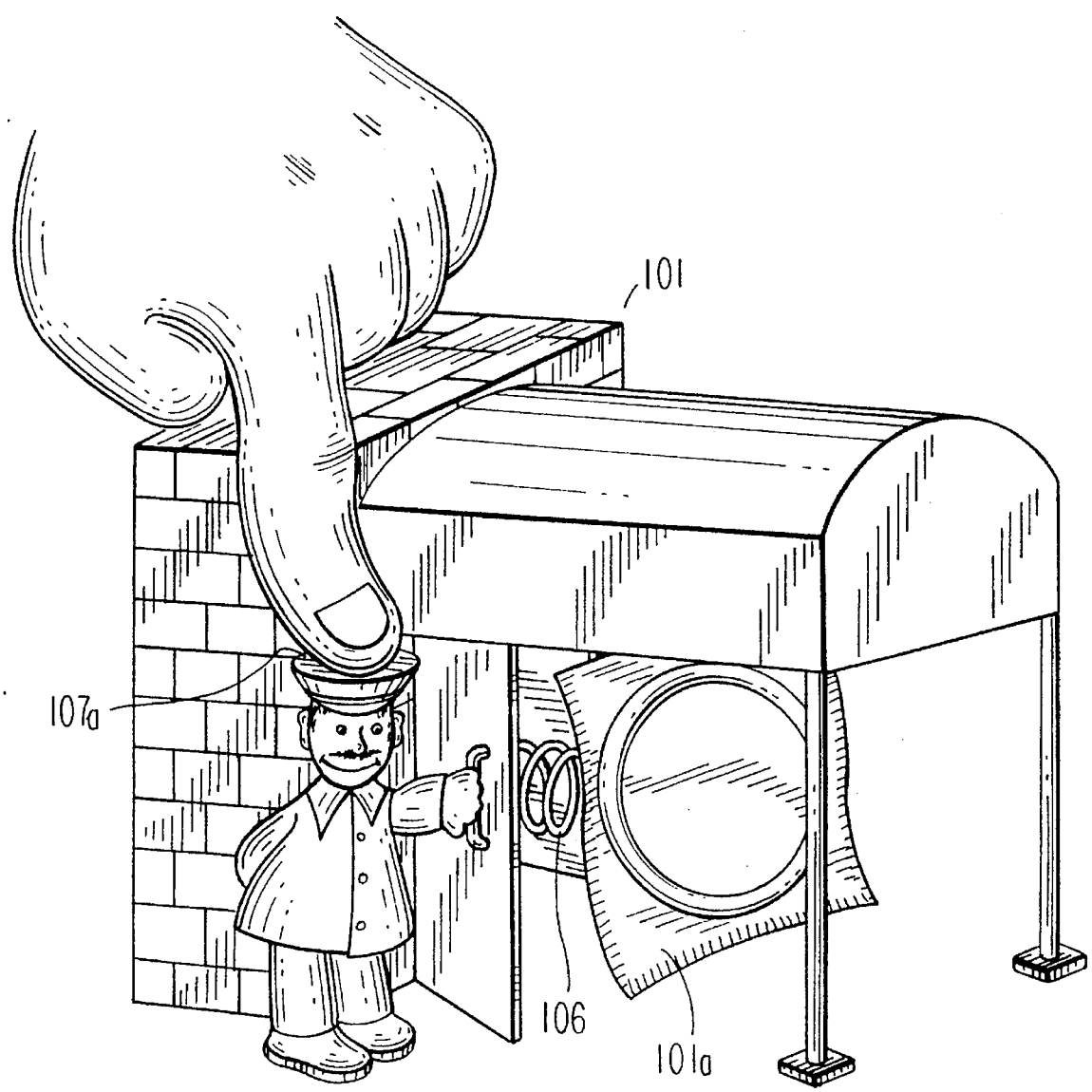
FIG. 11 is a perspective view of the embodiment shown in FIG. 10, shown being in use.
Figure 12:
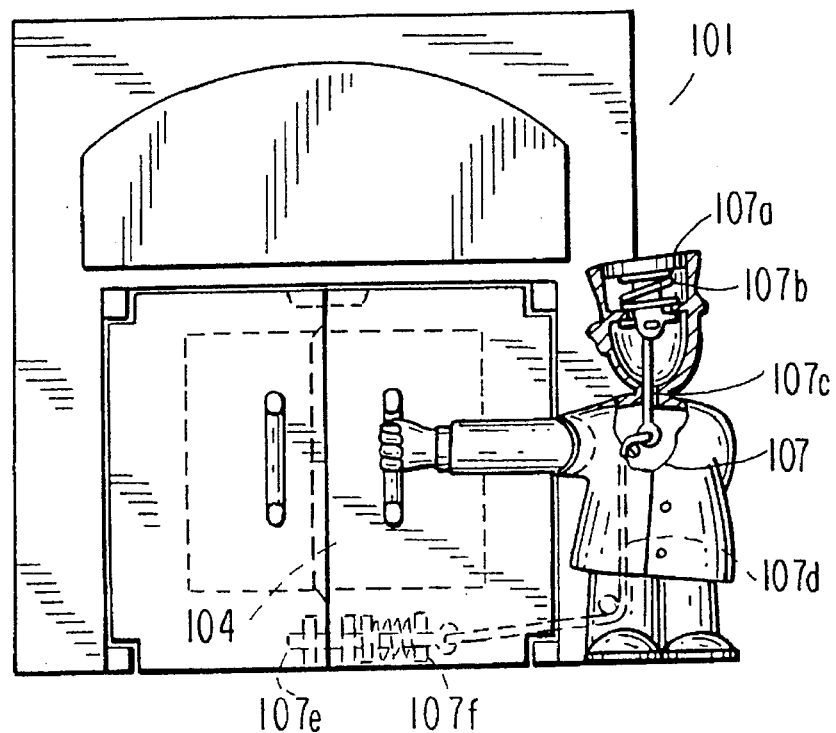
FIG. 12 is a rear view in partial section of the embodiment shown in FIG. 10.
Figure 13:
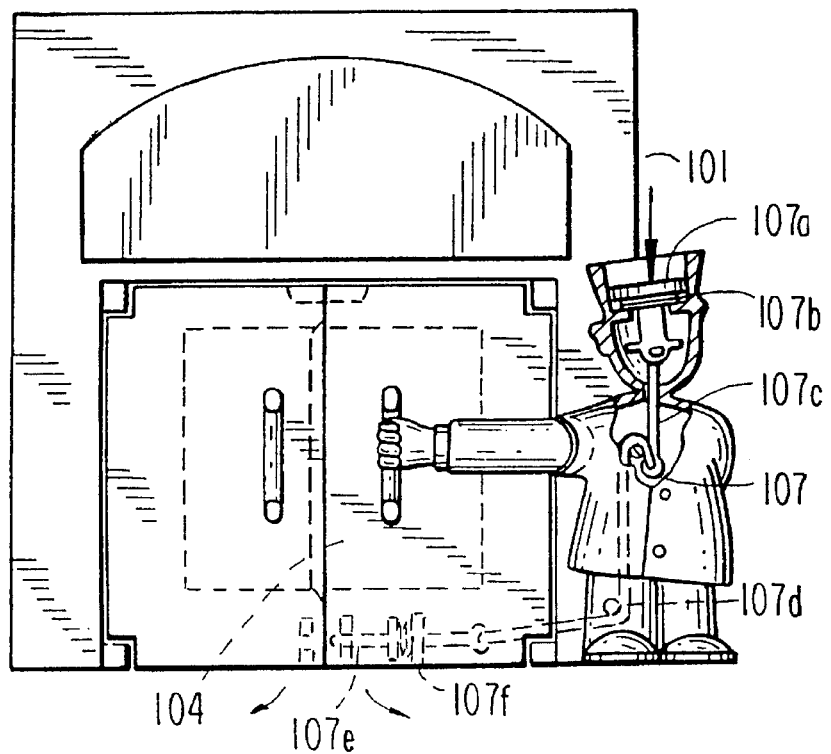
FIG. 13 is a rear view in partial section of the embodiment shown in FIG. 10, shown in use.

As shown in FIGS. 1–9, the present invention includes a dispenser 1 for releasing an object, such as a condom package 1a therefrom.

The dispenser 1 includes at least one magazine container compartment 2 with a dispenser opening 3 for a solid object, such as a condom, and an adjustable cover 4, such as a shutter, to the indicated extent for the desired dispensing of the condom package 1a.

Although other configurations may be used, in the embodiment shown in FIGS. 1–9, container compartment 2 may be a parallelopiped, such as in the shape of a small building, and adjustable cover 4 may be a movable door and container compartment 2.

In the version shown in FIGS. 1–9, dispenser 1 includes separate parts assembled as shown. Dispensing container compartment 2 includes at least one condom holder 5 attached to a spring portion 6, such as a coil spring, disposed to a handle release assembly 7. The dispensing spring portion 6 fits into a collar guide 8 within container compartment 2.

The condom package, which is generally smaller in size than cover opening 3, is housed in container 2 in at least one interior zone 9, such as zone space 9 between cover 4 and spring 6 in a coiled, loaded position.

Handle assembly 7 includes the release portion 7a, connected to pin 7b through guide tube 7c to restraining member 7d. When tab release 7a is withdrawn outward through guide tube 7c, pin 7b is released from restraining member 7d, thus also releasing condom package 1a and spring 6.

When opening 3 is closed by movable outer cover 4, such as a sealing shutter, condom 1a can be dispensed. By using the thumb and forefinger of one hand on the handle release assembly 7 disposed to movable outer cover 4 and pulling the handle release portion 7a, the condom 1a and spring 6 can be exposed for dispensing of condom 1a outward in a horizontal direction.

Other release mechanisms can be used. For example, as can be seen from drawing FIGS. 10–13, an alternate dispenser 101, such as a cabinet or other housing structure, includes a movable horizontal spring 106, which spring 106 is coupled with retaining handle portion 107, disposed to push button 107a, in order to cause a relatively quick movement of the condom package 101a. Push button 107a is attached above spring 107b to release pin 107c downward, thereby pulling flexible member 107d, such as a chain or elastic strap, and pin 107e, away from restraining member 107f, thus causing shutter 104 to open for release of spring 106 and condom package 101a.

In the preferred embodiment shown in FIGS. 1–9, the object 1a such as a condom, and the spring 6 are contained within container compartment 2 having a plurality of walls 12, 13, 14, and 15 with the particularity that, in this case, the rear portion 12 is contiguous to a collar 8 for spring 6, such that spring 6 expands outward from compartment container 2. At their respective horizontal levels, these walls 12, 13, 14, 15 are supported by the base 16, roof 17, and cantilateral porch 18, such that walls 12, 13, 14 and 15 remain fixed and stable in a strictly horizontal position adjacent to and contiguous with roof 17 and base 16.

Furthermore, on spring 6, condom holder 5 is mounted. In this case, condom holder 5 is used for holding condom 1a to be dispensed.

Obviously, starting from the aforementioned arrangement of dispenser 1, there are many possible structural constructions for obtaining the indicated function, all such constructions being equivalent. For example, embodiments as shown in the drawing, FIGS. 14–15, there is illustrated dispenser 201 having a spring such as in FIGS. 1–9. Displacement of spring 6 causes release of door cover 204 by moving handle release lever 207 connected to flexible member 207d, which moves away from a restraining member to release pin 207e, and therefore open cover 204.

Figure 14:
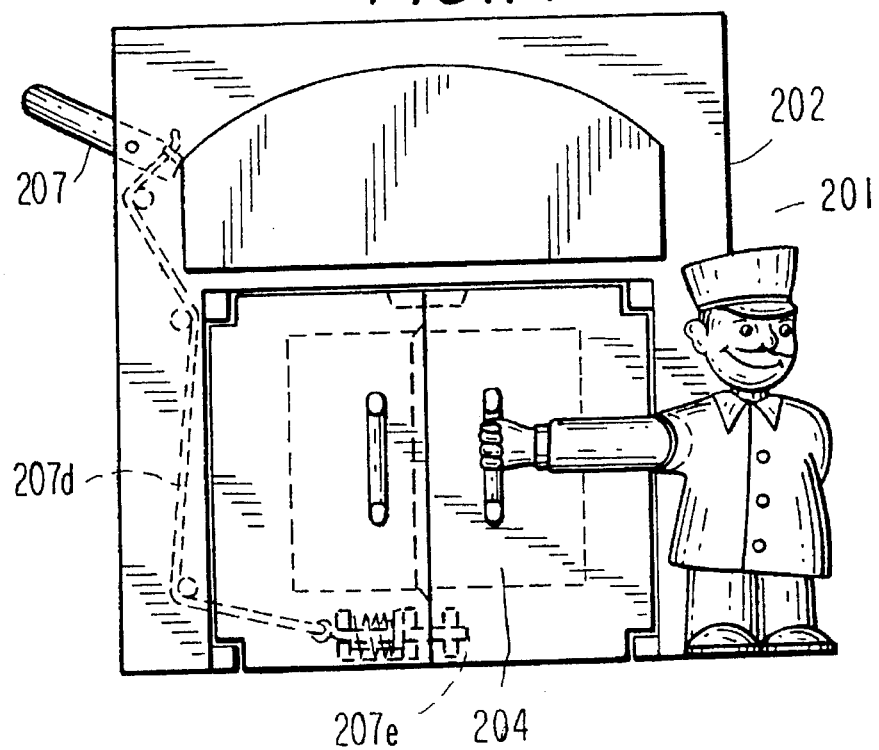
FIG. 14 is a front view of a further alternate embodiment wherein internal parts are shown in dotted lines.
Figure 15:
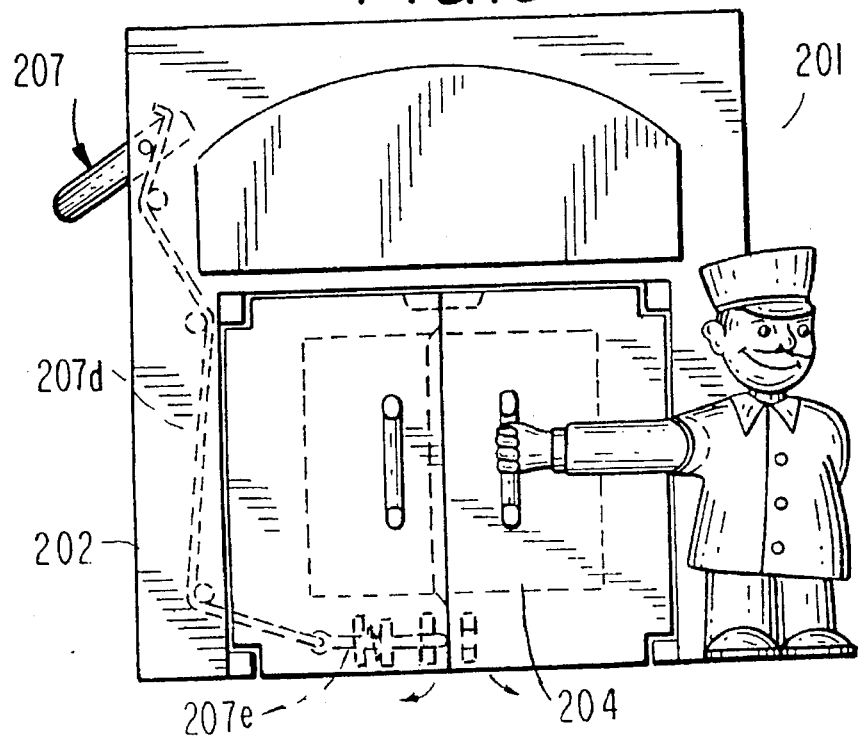
FIG. 15 is a front view of the further embodiment shown in FIG. 14, shown in use.

From an examination of the aforementioned enlarged detail shown in FIGS. 14–15, it can be understood that the spring 6 is sufficiently strong to project the condoms out of the dispenser.

As shown in FIGS. 14–15, it can be seen that the dispenser 201 includes a cabinet 202, which maintains the condom isolated inside.

According to this alternate embodiment, in the front part of cabinet 202 cover 204 opens to deliver the objects such as a condom package.

Figure 16:
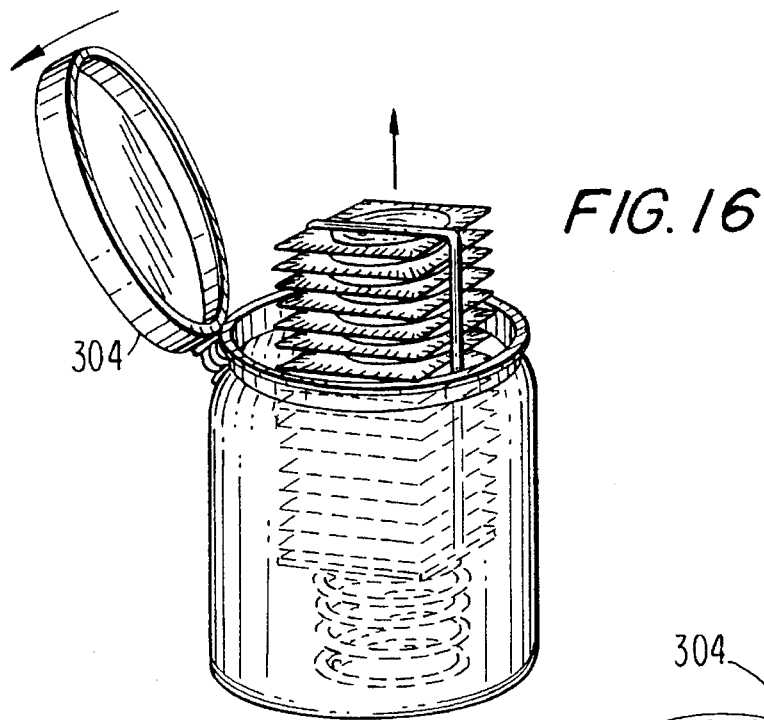
FIG. 16 is a perspective view of a second further embodiment of the present invention, shown in use.
Figure 17:
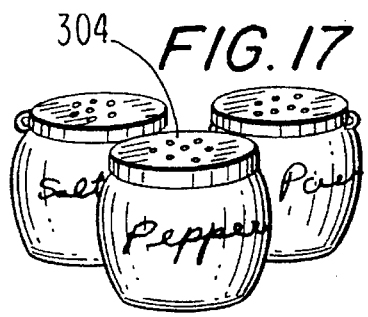
FIG. 17 is a perspective view of a plurality of the embodiment shown in FIG. 16.
Figure 18:
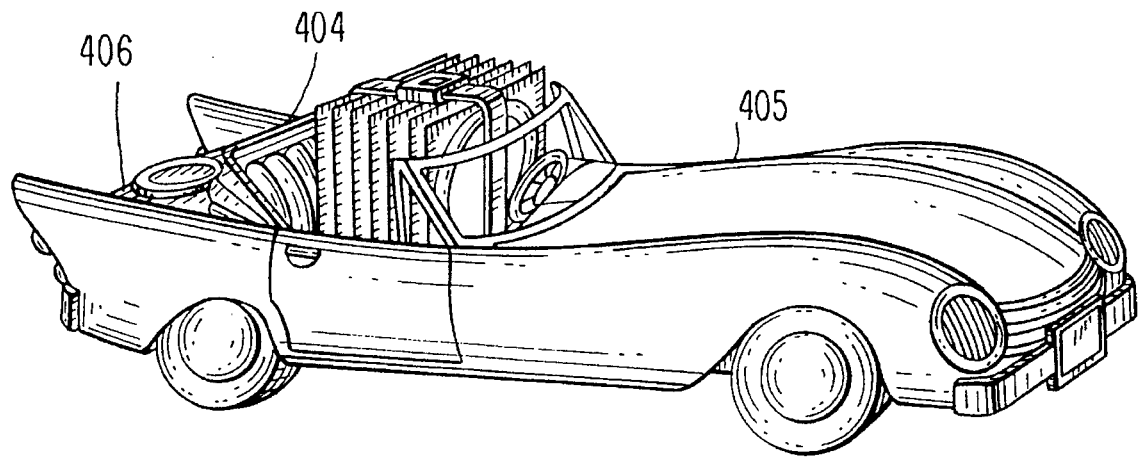
FIG. 18 is a perspective view of a third further embodiment of the present invention.

Referring again to the walls 12, 13, 14, 15, which walls 12, 13, 14, 15 present a parallelopipid shape; it is noted that the present invention is not limited to this configuration, but may have more or less other configurations, such as a jar or an automobile, as shown in FIGS. 16–17 and 18 respectively, wherein springs may open lid cover 304 for the jar or springs may open convertible roof 404, front hood 405 or rear back truck 406 respectively.

From these explanations it is clearly shown that the operation of the present invention is based on the dispensing movement thus explained, with the possibility for many other embodiments equivalent to those illustrated, for the various functions.

In the embodiments shown in FIGS. 18–26A,B,C the novelty dispenser may be a toy imitation motor vehicle, wherein the objects to be dispensed, such as condoms, are dispensed from the openable parts of the toy vehicle, such as from the trunk, the passenger compartment or the front engine compartment.

In the embodiments shown in FIGS. 19, 20, 21A and B, 22A and B, 23A and B and 24A and B, the hoods, roofs, or trunks are held shut by hammer latch B of vehicle V1.

Figure 26A:
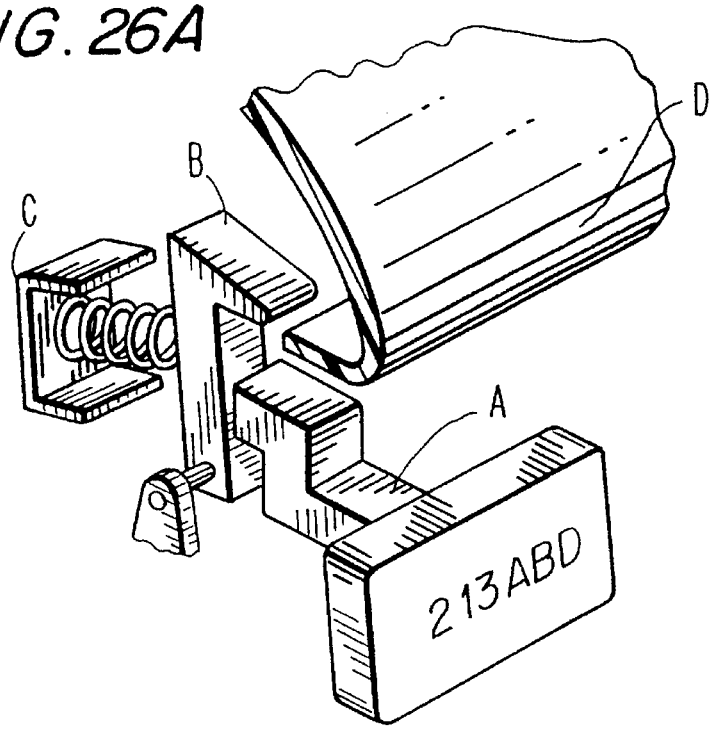
FIGS. 26A, 26B and 26C are closeup views of the latch portions of the present invention.
Figure 26B:
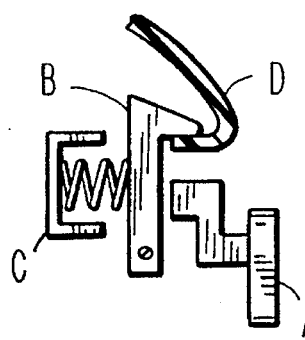
Figure 26C:
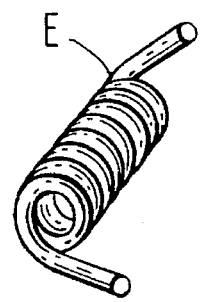

To open, as shown also in FIGS. 26A, 26B and 26C, when license plate button A is manually pushed in, it forces hammer latch B to pivot backwards, which releases latch D for the hood, roof or trunk. Pop up dispenser spring C forces hood H or trunk T open. In the case of a hood H, there is a second spring E which opens to its natural position to open hood H, and lessens the stress upon hood H as a result of the force of popup spring C.

To close hood H or trunk T, manual force is pushed down upon hood H or trunk T. Latch D slides down the angled top of hammer latch B, forcing it back just long enough to pop into place. Spring C forces hammer latch B to pivot back into place and lock hood H or trunk T in place.

In the embodiment shown in FIGS. 25A and 25B, rear push button A' located in the center of a simulated spare tire container on trunk T' of vehicle V2 is used to open hood H'. Button A' moves down into the body of vehicle V2, and pulls cord C', which is attached to the tip of button A'. Cord C' is pulled through hose conduit D', which conduit D' provides a smooth travel motion of cord C'. Cord C' in turn pulls back pivotable hammer latch E', freeing hood latch F'. Hood H' lifts open because of the action of hood spring G' and pop up dispenser spring H", to reveal the object stored, such as a condom CC in its translucent package holder.

When closing hood H', button spring B' returns button A' to its original position. Hammer spring E' pivots hammer latch E' closed and locks hood H' shut. Spring I urges hammer latch E' in place.

It is known that other modifications may be made to the present invention, without departing from the scope of the invention, as noted in the appended claims.

I claim:

1. A dispenser for convenient controlled dispensing of a solid object comprising:

a container in the shape of a hollow body incorporating a magazine compartment means for storing only a single said solid object for dispensing;

said hollow body having a dispenser opening extending along one side of said container;

door means mounted on said hollow body movable between a locked position closing said dispenser opening and a position exposing said dispenser opening;

means within said magazine compartment means for holding said solid object in a position restrained by said door means when in the locked position including a spring for biasing said holding means against said solid object, said solid object pushing said door means when unlocked into the position exposing said dispenser opening and being discharged from said hollow body;

handle assembly means extending from said container comprising a movable handle for unlocking said door means to permit said holding means to push said solid object out through said dispenser opening thereby dispensing said solid object from said container said movable handle permitting a user to open said container for dispensing the solid object from said container; and storage means separated from said magazine compartment means for storing additional solid objects for placement in said magazine compartment means when said magazine compartment means is empty due to release of the solid object within said magazine compartment means.

2. The dispenser of claim 1, wherein said hollow body for containing a solid object is a parallelopiped.

3. The dispenser of claim 1, wherein said hollow body is an elongated substantially cylindrical jar and further wherein said outer cover is a substantially cylindrical shape, above said hollow body.

4. The dispenser of claim 1 wherein said body comprises the shape of a building, said handle assembly means further comprising a door man having an arm extending to a handle mounted on said door means, said movable handle being a button built into the head of said door man, the depressing of said button causing the unlocking of said door means.

5. The device of claim 1, wherein said body comprises a shape of a motor vehicle.

6. The device of claim 1, wherein said body comprises a substantially square cross-sectional shape.

7. The dispenser as in claim 1 wherein said solid object is a condom package.

8. A novelty toy dispenser for objects, comprising:

a hollow container body, said container body having a hinged movable cover comprising an imitation automobile hood enclosing a magazine compartment therein, said cover openable by the depressing of a button engagable with a latch communicating with a spring, said spring responsive to opening said at least one cover, exposing the object in said magazine compartment.

9. A novelty toy dispenser for objects, comprising:

a hollow container body, said container body having at least one hinged movable cover comprising an imitation automobile hood enclosing a magazine compartment therein, said body having a depressable button connected by a cord within a conduit communicating with a pivotable hammer latch movable between an openable and a closable position, said latch releasing said at least one cover to expose the object in said magazine compartment.

10. The novelty dispenser as in claim 8 wherein said button is in the form of a replica of a part of a motor vehicle.

11. A novelty toy dispenser for objects, comprising:

a hollow container body, said container body having a hinged movable cover comprising an imitation automobile trunk cover enclosing a magazine compartment therein, said cover openable by the depressing of a button engagable with a latch communicating with a spring, said spring responsive to opening said at least one cover, exposing the object in said magazine compartment.

12. A novelty toy dispenser for objects, comprising:

a hollow container body, said container body having a hinged movable cover comprising an imitation convertible automobile retractable roof enclosing a magazine compartment therein;

said cover openable by the depressing of a button engagable with a latch communicating with a spring, said spring responsive to opening said at least one cover, exposing the object in said magazine compartment.

13. A novelty toy dispenser for objects, comprising:

a hollow container body, said container body having at least one hinged movable cover comprising an imitation automobile trunk cover enclosing a magazine compartment therein, said body having a depressable button connected by a cord within a conduit communicating with a pivotable hammer latch movable between an openable and a closable position, said latch releasing said at least one cover to expose the object in said magazine compartment.

14. A novelty toy dispenser for objects, comprising:

a hollow container body, said container body having at least one hinged movable cover comprising an imitation automobile retractable roof enclosing a magazine compartment therein, said body having a depressable button connected by a cord within a conduit communicating with a pivotable hammer latch movable between an openable and a closable position, said latch releasing said at least one cover to expose the object in said magazine compartment.

15. A novelty toy dispenser for objects, comprising:

a hollow container body, said container body having at least one hinged movable cover enclosing a magazine compartment therein, said body having a depressable button in the form of a replica of a part of a motor vehicle connected by a cord within a conduit communicating with a pivotable hammer latch movable between an openable and a closable position, said latch releasing said at least one cover to expose the object in said magazine compartment.

\* \* \* \* \*